US012618079B2

(12) United States Patent
Giacomelli et al.

(10) Patent No.: US 12,618,079 B2
(45) Date of Patent: May 5, 2026

(54) POWDERY MILDEW RESISTANT GRAPEVINE PLANT

(71) Applicants: SciENZA Biotechnologies 4 B.V., Enkhuizen (NL); Fondazione Edmund Mach, San Michele all'Adige (IT)

(72) Inventors: Lisa Giacomelli, San Michele all'Adige (IT); Tieme Zeilmaker, Enkhuizen (NL); Claudio Moser, San Michele all'Adige (IT); Jeroen Nicolaas Albert Maria Rouppe Van Der Voort, Enkhuizen (NL)

(73) Assignees: Fondazione Edmund Mach, San Michele all'Adige (IT); SciENZA Biotechnologies 4 B.V., Enkhuizen (NL)

( * ) Notice: Subject to any disclaimer, the term of this patent is extended or adjusted under 35 U.S.C. 154(b) by 433 days.

(21) Appl. No.: 18/010,819

(22) PCT Filed: Jun. 18, 2020

(86) PCT No.: PCT/EP2020/067007
§ 371 (c)(1),
(2) Date: Dec. 16, 2022

(87) PCT Pub. No.: WO2021/254629
PCT Pub. Date: Dec. 23, 2021

(65) Prior Publication Data
US 2023/0227840 A1 Jul. 20, 2023

(51) Int. Cl.
*C12N 15/82* (2006.01)
*A01H 6/88* (2018.01)

(52) U.S. Cl.
CPC ........... *C12N 15/8282* (2013.01); *A01H 6/88* (2018.05)

(58) Field of Classification Search
CPC .............................. C12N 15/8282; A01H 6/88
See application file for complete search history.

(56) References Cited

U.S. PATENT DOCUMENTS 11,441,157 B2 9/2022 Malnoy et al.

FOREIGN PATENT DOCUMENTS

WO 2017005747 A1 1/2017

OTHER PUBLICATIONS

Wan DY, Guo Y, Cheng Y, Hu Y, Xiao S, Wang Y, Wen YQ. CRISPR/Cas9-mediated mutagenesis of VvMLO3 results in enhanced resistance to powdery mildew in grapevine (*Vitis vinifera*). Hortic Res. Aug. 1, 2020;7:116. doi: 10.1038/s41438-020-0339-8. PMID: 32821399; PMCID: PMC7395163. (Year: 2020).*

(Continued)

*Primary Examiner* — Amjad Abraham
*Assistant Examiner* — Dequantarius Javon Speed
(74) *Attorney, Agent, or Firm* — The Webb Law Firm

(57) ABSTRACT

Provided herein are powdery mildew-resistant grapevine plants and methods for providing powdery mildew resistance to susceptible grapevine plants. Specifically, provided herein are grapevine plants including in their genome an impaired *Erysiphe necator* resistance-conferring gene, wherein the corresponding not impaired *Erysiphe necator* resistance conferring resistance-conferring gene designated VvMLO13 encodes a protein including the amino acid sequence of SEQ ID No. 1, or proteins having 95% sequence identity therewith. The impairment results in an absence of a protein comprising the amino acid sequence of SEQ ID No. 1, or proteins having 95% sequence identity therewith, in the grapevine plant and wherein the grapevine plant is resistant to powdery mildew.

7 Claims, 4 Drawing Sheets

Specification includes a Sequence Listing.

Wild type mlo13

(56) References Cited

OTHER PUBLICATIONS

NCBI Reference Sequence: XM_002282180.4. Bethesda (MD): National Library of Medicine (US), National Center for Biotechnology Information. 2016. Available from: https://www.ncbi.nlm. nih.gov/nuccore/XM_002282180.4 (Year: 2016).*

Giacomelli, L., Zeilmaker, T., Malnoy, M., Rouppe van der Voort, J., & Moser, C. (Jul. 2018). Generation of mildew-resistant grapevine clones via genome editing. In XII International Conference on Grapevine Breeding and Genetics, 1248 (pp. 195-200). (Year: 2018).*

Karakas, B., Weeraratna, A. T., Abukhdeir, A. M., Konishi, H., Gustin, J. P., Vitolo, M. I., . . . & Park, B. H. (2007). P21 gene knock down does not identify genetic effectors seen with gene knock out. Cancer biology & therapy, 6(7), 1025-1030. (Year: 2007).*

Feechan et al., "Identification of grapevine MLO gene candidates involved in susceptibility to powdery mildew", Functional Plant Biology, 2008, pp. 1255-1266, vol. 35.

Malnoy et al., "DNA-Free Genetically Edited Grapevine and Apple Protoplast Using CRISPR/Cas9 Ribonucleoproteins", Frontiers in Plant Science, Dec. 2016, pp. 1-9, vol. 7:1904.

Pessina et al., "Knockdown of MLO genes reduces susceptibility to powdery mildew in grapevine", Holticulture Research, 2016, pp. 1-9, vol. 3.

"Technical questionnaire: *Vitis* L.", Rete Di Imprese Italian Variety Club (IVC), Community Plant Variety Office, 2020, pp. 1-7.

* cited by examiner

Wild type mlo13 mlo13

Wild type

| Wild type | mlo13 |

POWDERY MILDEW RESISTANT GRAPEVINE PLANT

CROSS REFERENCE TO RELATED APPLICATION

This application is the United States national phase of International Patent Application No. PCT/EP2020/067007 filed Jun. 18, 2020, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2208066_ST25.txt. The size of the text file is 29,578 bytes, and the text file was created on Dec. 6, 2022.

BACKGROUND OF THE INVENTION

Field of the Invention

The present invention relates to powdery mildew resistant grapevine plants (*Vitis* spp.) and to methods and means for providing the present powdery mildew resistance to powdery mildew susceptible grapevine plants and to methods and means for providing the present powdery mildew resistant grapevine plants.

Description of Related Art

*Erysiphe necator*, also designated as Uncinula necator, is a fungus that causes powdery mildew disease symptoms in grapevine plants. The fungus is a common pathogen for *Vitis* species of which the most important species is *Vitis vinifera*.

Grapevine plants require large amounts of pesticides, particularly fungicides, to prevent yield losses. Between 1992 and 2003, 73% of the fungicides sold in France, Italy, Spain and Germany, were used for grapevine protection, a crop that covers only 8% of the land used for agriculture in the considered countries (EUROSTAT, 2007).

Grapevine powdery mildew (PM) caused by the fungus *Erysiphe necator*, is one of the most economically relevant diseases of grapevine worldwide. *Erysiphe necator* is an obligate biotroph that can infect all green tissues of grapevine and causes significant losses in yield and berry quality. PM symptoms include a white or grey powder covering of the upper and lower surfaces of the leaves. Fruit infections result in shriveling or cracking of the berries. The quality of the fruit is severely damaged, with increased acidity and decreased anthocyanin and sugar content.

Powdery mildew is controlled with frequent applications of chemical fungicides. However, the intense application of chemical fungicides has several drawbacks. First of all, the effects on the environment of fungicides are well documented. Secondly, the costs of the chemicals and their applications can reach up to 20% of the total expenses for grape production in some areas. Thirdly, the development of resistant populations of the pathogen was already documented by Baudoin et al. (2008) and Dufour et al. (2011), strongly reducing the efficacy of chemical treatments. Therefore, there is increasing interest in the development of new alternative methods to chemical treatments.

The generation of PM-resistant varieties is one of the best options to make sustainable grapevine cultivation a realistic possibility, preserving at the same time the incomes of the growers. A study carried out on "Chardonnay" production in California, showed that the use of a PM-resistant variety could save the growers around $720 per hectare, with a significant reduction of fungicide usage (Fuller et al., 2014).

Most cultivars of the European grapevine (*Vitis vinifera*), which includes the world's finest and most widely planted wine and table grapevine cultivars, are highly susceptible to PM (Gadoury et al. 2003). In contrast, North American *Vitis* species co-evolved with *E. necator* and possess various levels of resistance to the pathogen (Fung et al., 2008). This resistance could be introgressed by crossing *Vitis vinifera* with one of the resistant American *Vitis* species, but breeding is a slow process in grapevine and the acceptance of resistant hybrids by producers and consumers has been limited in the past (Fuller et al., 2014). The use of technologies like genetic transformation or high-throughput marker-assisted selection can be used to obtain resistant grapevine cultivars with desirable grape properties for producers and consumers (Feechan et al., 2013a).

The most common strategy to develop resistant plants is focused on the introgression of resistance genes (R-genes). R-genes encode proteins that recognize pathogen effectors and trigger a defense response, mediated by a signaling network in which plant hormones play a major role (Pavan et al., 2010). Resistance is manifested as a localized hypersensitive response at the site of infection (Bari and Jones, 2009). Resistance conferred by R-genes is scarcely durable, as mutations of pathogen effectors allow it to overcome resistance (Parlevliet et al., 1993).

An alternative approach is based on the inactivation of susceptibility genes (S-genes), defined as genes whose loss-of-function results in recessively inherited resistance (Pavan et al., 2010). Some pathogens are able to suppress plant defense by activating plant proteins whose function is the negative regulation of plant immunity system. The genes encoding these plant proteins are known as susceptibility genes (S-genes) and their knock-out releases the suppression of plant defense and leads to resistance (Pavan et al., 2010). The disadvantage of S-genes is the pleiotropic phenotypes sometimes associated to their knock-out (Pavan et al. 2011).

Mildew Locus O (MLO) genes are a typical example of PM S-genes. Resistance due to the knock-out of an MLO gene (mlo resistance) was discovered in barley in 1992 (Jørgensen, 1992) and for a long time was considered as a unique form of resistance. However, further studies revealed that MLO genes are largely conserved across the plant kingdom and their loss-of-function resulted in resistance in several species, such as *Arabidopsis* (Consonni et al., 2006), pea (Pavan et al., 2011), tomato (Bai et al., 2008), and pepper (Zheng et al., 2013). Not all MLO genes are S-genes and MLO family members are divided in seven clades (Acevedo-Garcia et al., 2014; Pessina et al., 2014). Only two clades contain S-genes: clade IV contains all monocots S-genes (Panstruga et al., 2005; Reinstädler et al., 2010); and clade V contains all dicots S-genes (Consonni et al., 2006; Bai et al., 2008; Feechan et al., 2008; Winterhagen et al., 2008). Not all the members of clades IV and V are S-genes.

International patent application WO 2017/005747 discloses four MLO genes designated VvMLO6, VvMLO7, VvMLO11 and VvMLO13. According to WO 2017/005747, VvMLO7 is a major powdery mildew resistance providing gene while VvMLO6 and VvMLO11 are identified as genes providing additive resistance. WO 2017/005747 discloses that downregulation of VvMLO13 expression does not provide powdery mildew resistance in grapevine.

Considering the economic impact of an *Erysiphe necator* infection on grape production, there is a continuing need in the art for *Erysiphe necator* resistance providing genes.

SUMMARY OF THE INVENTION

It is an objective of the present invention, amongst other objectives, to meet this need of the art.

According to the present invention, the above objective, amongst other objectives, is met by providing impaired *Erysiphe necator* resistance providing genes as outlined in the appended claims.

Specifically, the above objective, amongst other objectives, is met according to a first aspect of the present invention by a grapevine plant (*Vitis* spp.) comprising in its genome an impaired *E. necator* resistance-conferring gene, wherein the corresponding not impaired *E. necator* resistance-conferring gene designated VvMLO13 encodes a protein comprising the amino acid sequence of SEQ ID No. 1, or proteins having 95% sequence identity therewith, wherein the impairment results in an absence of a protein comprising the amino acid sequence of SEQ ID No. 1, or proteins having 95% sequence identity therewith, in said grapevine plant and wherein the grapevine plant is resistant to powdery mildew.

The present inventors have surprisingly discovered that despite prior art disclosures that VvMLO13 is not a powdery mildew resistance providing gene, absence of expression of this gene provides substantially complete resistance against *Erysiphe necator* in grapevine, i.e. the leaves of grapevine are substantially free of powdery mildew sporulation.

Within the context of the present invention, a grapevine is considered to be resistant to powdery mildew when detached leaves of a grapevine stem at a growth stadium of 7 to 11 leaves per stem show less than 10%, such as less than 9%, 8%, 7%, 6%, 5%, 4%, 3%, 2%, 1% or 0% sporulation as compared to wild-type leaves at 5 to 15 dpi infection with *Erysiphe necator*.

Without wishing to be limited to an underlying mechanism of the powdery mildew resistance observed, the presently disclosed powdery mildew resistance based on VvMLO13 appears to be due to a complete reduction of expression of VvMLO13 of both alleles (2n) either by complete disruption of transcription or mutation of the proteins encoded by both alleles rendering these proteins no longer capable of performing their function in grapevine.

Accordingly, the present invention, according to a preferred embodiment, relates to grapevine plants, wherein the absence of a protein comprising the amino acid sequence of SEQ ID No. 1 results from one or more mutations in the nucleotide sequence of a cDNA comprising SEQ ID No. 2.

Alternatively, the present invention, according to a preferred embodiment, relates to grapevine plants, wherein the absence of a protein comprising the amino acid sequence of SEQ ID No. 1 results from one or more mutations in the not impaired *E. necator* resistance-conferring gene designated VvMLO13 resulting in an absence of expression thereof.

According to the present invention, the present one or more mutations comprise deletions, insertions or substitutions in the nucleotide sequence of a cDNA comprising SEQ ID No. 2. Examples of such mutations are 1 or 2 base pair deletions or insertions in SEQ ID No. 2 causing frameshifts, base pair changes resulting in a triplet coding another amino acid, i.e. amino acid substitutions or deletion of a triplet.

According to another preferred embodiment, the present invention relates to grapevine plants, wherein the absence of a protein comprising the amino acid sequence of SEQ ID No. 1 results from the impaired *E. necator* resistance-conferring gene to encode a nucleotide sequence comprising SEQ ID No. 3 (1 base pair deletion in SEQ ID No. 2), SEQ ID No. 4 (triplet deletion in SEQ ID No. 2), or SEQ ID No.

5 (1 base pair insertion in SEQ ID No. 2), or combinations thereof or a protein comprising an amino acid sequence comprising SEQ ID No. 6 (encoded by SEQ ID No. 3), SEQ ID No. 7 (encoded by SEQ ID No. 4), or SEQ ID No. 8 (encoded by SEQ ID No. 5), or combinations thereof.

According to an especially preferred embodiment, the present invention relates to grapevine plants wherein the absence of a protein comprising the amino acid sequence of SEQ ID No. 1 results from the impaired *E. necator* resistance-conferring gene (2n) encoding a nucleotide sequence comprising SEQ ID No. 3 and SEQ ID No. 4, SEQ ID No. 3 and SEQ ID No. 5, SEQ ID No. 4 and SEQ ID No. 5, SEQ ID No. 3 and SEQ ID No. 3, SEQ ID No. 4 and SEQ ID No. 4, SEQ ID No. 5 and SEQ ID No. 5.

The present grapevine plants further preferably comprise in their genome one or more *E. necator* resistance-conferring genes, preferably one or more *E. necator* resistance-conferring genes selected from the group consisting of VvMLO6, VvMLO7 and VvMLO11.

The present invention also relates to methods for providing a powdery mildew resistant grapevine plant, the methods comprising the step of mutating a gene designated VvMLO13 to encode a protein comprising the amino acid sequence of SEQ ID No. 1 in a powdery mildew susceptible grapevine plant. The present methods preferably comprise mutating a gene designated VvMLO13 to encode a protein comprising the amino acid sequence of SEQ ID No. 1 by introducing a deletion, insertion, or substitution in a cDNA sequence comprising SEQ ID No. 2.

The present invention additionally relates to seeds, fruits or plant parts of the present grapevine plant.

The present invention further relates to impaired powdery mildew resistance-conferring genes designated VvMLO13, wherein the impaired powdery mildew resistance-conferring genes encode a protein comprising an amino acid sequence selected from the group consisting of SEQ ID No. 6, SEQ ID No. 7 and SEQ ID No. 8, powdery mildew resistance providing proteins, the proteins comprise an amino acid sequence selected from the group consisting of SEQ ID No. 6, SEQ ID No. 7 and SEQ ID No. 8 and use thereof for introducing or identifying powdery mildew resistance in a grapevine plant.

BRIEF DESCRIPTION OF THE DRAWINGS

The present invention will be further detailed in the example below. In the example, reference is made to figures wherein.

DESCRIPTION OF THE INVENTION

Example

Material and Methods

Leaves to be tested in a detached-leaf-assay were taken from grapevine plants grown in pots until they reached a stage of at least 8-10 leaves per stem. From the top of each stem, the second, third and fourth leaf were used as test leaves. They were surface-sterilized in a bath of 1% bleach for 2 minutes, and then rinsed three times in sterile water, by soaking them for two minutes, and then left to dry in sterile conditions (laminar flow hood).

A 1% agar layer of about 1 cm was poured in a sterile plastic box, or sterile plates, and then covered by sterile filter paper. Test leaves were laid on the paper ensuring that the petiole is sticking in the underneath agar layer. Using a PM infected leaf with visible sporulation on its surface as inoculum, *E. necator* spores were distributed on the test leaves by the aid of an air pump.

Box/plates were covered by a lid and stored in a growth chamber with the following settings: 16 hour light period, 21° C. and 21% RH. Scoring was performed at several timepoints indicated in the figures by calculating the surface area of leaves covered by powdery mildew or making pictures of the leaves.

PM hyphae were visualized by aniline blue coloration on infected leaves previously treated with ethanol: (glacial) acetic acid 3:1 as described in detail in "Pessina et al., (2016)". Leaf sections were mounted on glass slides and observed with a microscope Leica MZ16F.

Results

Mutant plants were generated by *Agrobacterium*-mediated transformation of young embryogenic calli of cv. Crimson seedless. Binary vectors constitutively expressing the CRISPR/Cas9 machinery were used to specifically target VvMLO13. Plants regenerated from such calli were then selected for kanamycin resistance and their DNA analyzed by next-generation sequencing (Illumina®).

Plants were obtained edited in MLO13 after NextGen sequencing confirmation (minimal sequencing depth 1000× coverage). Several mlo13 alleles were obtained after sequencing and used for these experiments. The mlo13 mutant used in experiment 1 is biallelic with 1 base pair insertion for one allele and 1 base pair deletion for the other allele both causing frame shift mutations. For experiment 2, another mlo13 was used, this mutant contains a 3 base pair deletion for one allele and a 1 base pair deletion for the other allele.

Detached leaves from Crimson seedless were used in a PM assay as described in the M & M section.

Figure 1:
FIG. 1: shows the results of a PM assay on detached leaves of wild type and mlo13 plants. Wild type leaves show complete sporulation, mlo13 leaves are clean of PM sporulation at 14 dpi.
Figure 2:
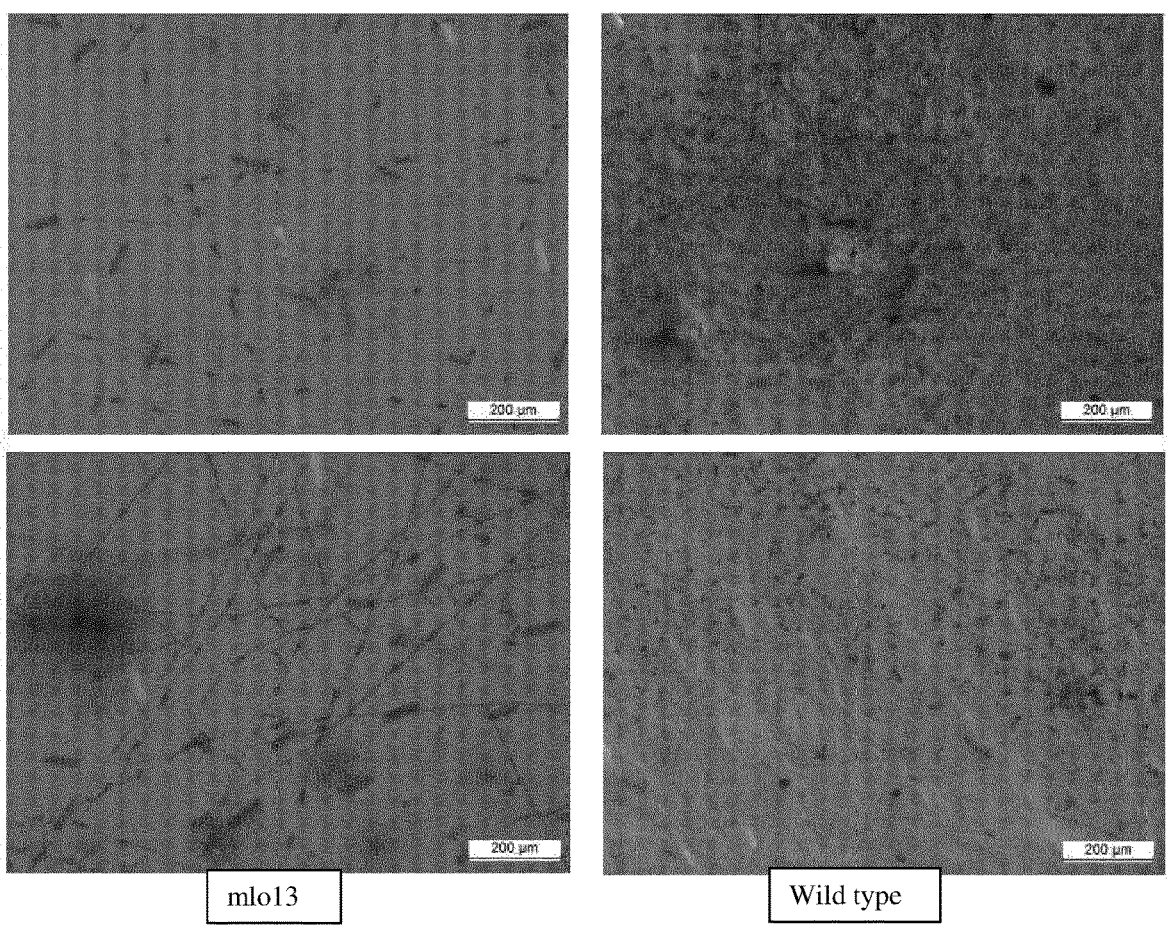
FIG. 2: shows hyphal growth of PM visualized using specific staining on a microscopic image. PM infection on leaves at 14 dpi in the wild type (on the right) and the mlo13 mutant (on the left). There is clearly less hyphal growth in the mutant compared to its wild type.

Experiment 1:

FIG. 1 shows 2 detached leaves of wild type and mlo13 mutant plants. Whereas the wild type shows PM sporulation, the mlo13 mutant does not show any sporulation. Picture was taken at 14 dpi. To further analyze the phenotype of the wild type and mlo13 mutants, histological analysis was performed on the same leaf material by visualizing PM hyphae using aniline blue. As seen in FIG. 2, in the wild type hyphae are present all over the leaf surface where they form dense structures, while on the mlo13 mutant, they are only visible in a limited number. This clearly illustrates that the mlo13 hardly supports pathogen growth.

Figure 3:
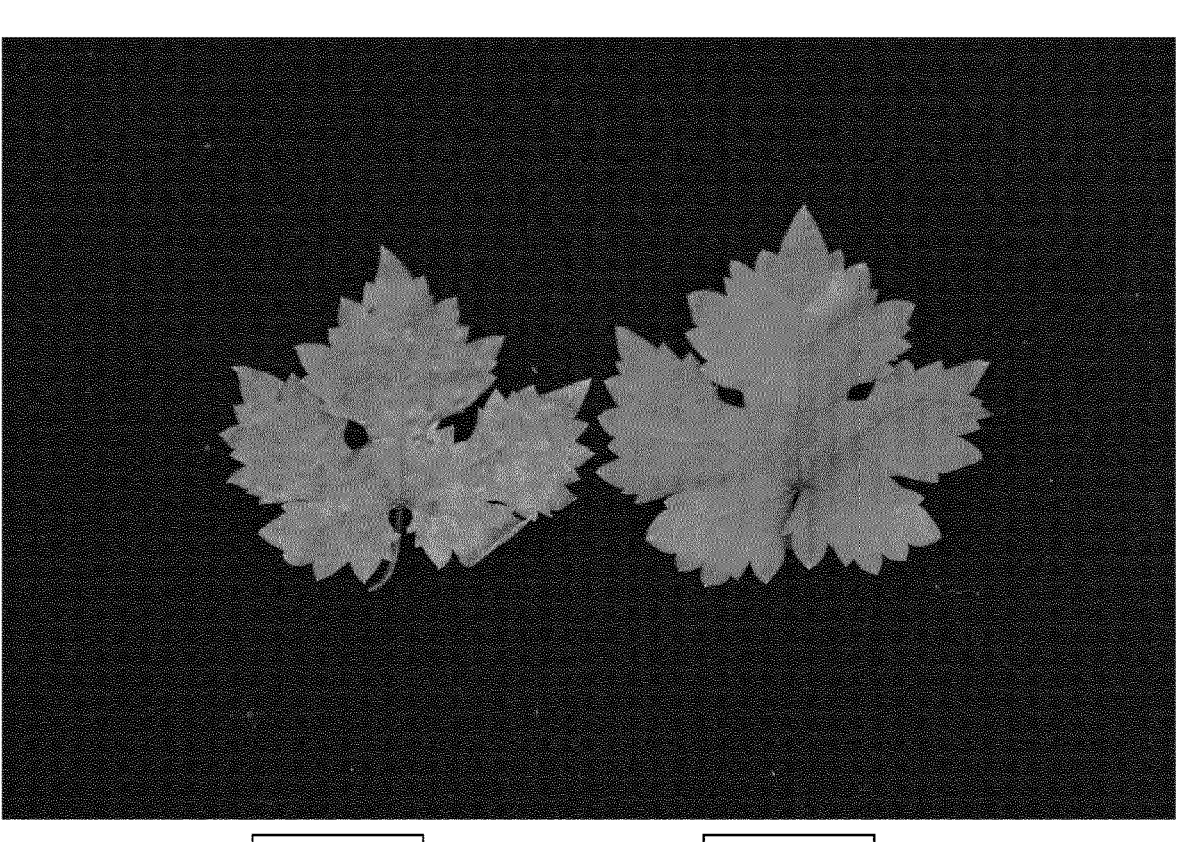
FIG. 3: shows a PM assay on detached leaves of wild type (on the left) and mlo13 leaves (on the right). Wild type leaves show complete sporulation, mlo13 leaves are clean of PM sporulation at 13 dpi.
Figure 4:
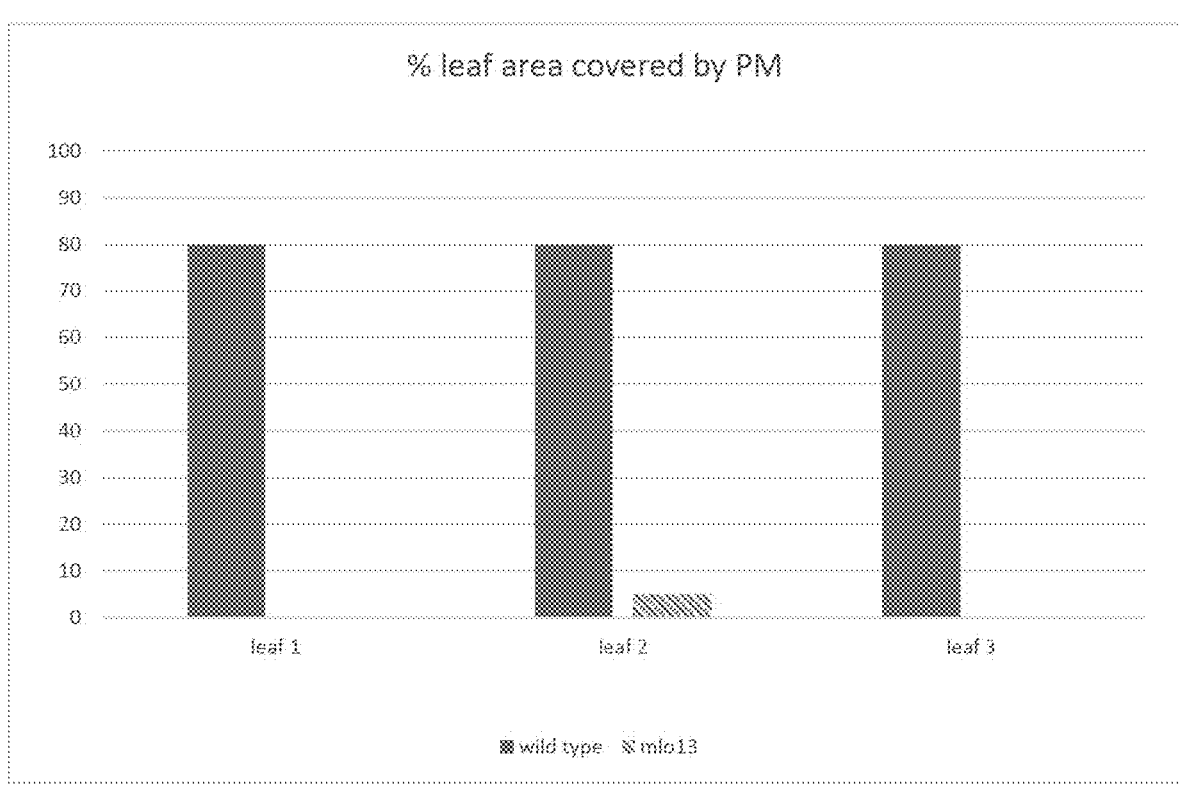
FIG. 4: shows quantification of PM sporulation in wild type and mlo 13 mutant leaves. Percentage of leaf area covered by PM sporulation was determined for 3 wild type leaves and 3 mlo13 leaves 10 dpi.

Experiment 2:

FIG. 3 shows an example of wild type leaf and mlo13 leaf that were used in a PM assay. Picture of the leaves were taken 10 dpi and show severe sporulation on the wild type leaf. The mlo13 mutant is resistant to PM as seen by the strongly reduced or absence of sporulation. To further analyze this, 3 wild type leaves and 3 mlo13 leaves were used for quantitative analysis. FIG. 4 shows percentage of the leaf area covered with PM sporulation for 3 wild type leaves and 3 mlo13 mutant leaves. Wild type leaves have at least 80% of the surface area covered in PM sporulation while in the mlo13 this was absent or greatly reduced to a maximum of 5% of the surface area.

The invention claimed is:

1. A powdery mildew-resistant grapevine plant comprising in its genome a mutation in a gene having the nucleotide sequence of SEQ ID No. 2, wherein the mutation results in the absence of a protein comprising the amino acid sequence of SEQ ID No. 1, or a protein having 95% sequence identity therewith, and confers resistance to *Erysiphe necator* in said grapevine plant.

2. The grapevine plant according to claim 1, wherein the alleles of the gene with the mutation have the nucleotide sequences of SEQ ID No. 3, SEQ ID No. 4, and/or SEQ ID No. 5.

3. The grapevine plant according to claim 2, wherein the plant comprises in its genome two alleles selected from the group consisting of SEQ ID No. 3 and SEQ ID No. 4, SEQ ID No. 3 and SEQ ID No. 5, SEQ ID No. 4 and SEQ ID No. 5, SEQ ID No. 3 and SEQ ID No. 3, SEQ ID No. 4 and SEQ ID No. 4, or SEQ ID No. 5 and SEQ ID No. 5.

4. The grapevine plant according to claim 1, wherein the grapevine plant further comprises in its genome one or more

*Erysiphe necator* resistance-conferring genes selected from the group consisting of VvMLO6, VvMLO7 and VvMLO11.

5. A method for providing a powdery mildew-resistant grapevine plant, comprising mutating a gene having the nucleotide sequence of SEQ ID No. 2, wherein the mutation results in the absence of a protein comprising the amino acid sequence of SEQ ID No. 1, or a protein having 95% sequence identity therewith, in a powdery mildew-susceptible grapevine plant, thereby providing a grapevine plant that is resistant to powdery mildew.

6. The method for providing a powdery mildew-resistant grapevine plant according to claim 5, wherein the step of mutating the gene encoding a protein comprising the amino acid sequence of SEQ ID No. 1 comprises introducing a deletion, insertion, or substitution in an endogenous sequence comprising the nucleotide sequence of SEQ ID No. 2.

7. A seed, fruit, or plant part of a grapevine plant according to claim 1.

* * * * *

```
                        SEQUENCE LISTING

<160> NUMBER OF SEQ ID NOS: 8

<210> SEQ ID NO 1
<211> LENGTH: 586
<212> TYPE: PRT
<213> ORGANISM: Vitis vinifera

<400> SEQUENCE: 1

Met Ala Gly Ala Thr Gly Gly Arg Ser Leu Glu Gln Thr Pro Thr Trp
1               5                   10                  15

Ala Val Ala Val Val Cys Phe Val Leu Val Leu Ile Ser Ile Ile Ile
            20                  25                  30

Glu Tyr Ile Ile His Leu Thr Gly Lys Trp Leu Lys Lys Lys His Lys
        35                  40                  45

Arg Ala Leu Tyr Glu Ala Leu Glu Lys Val Lys Ser Glu Leu Met Leu
    50                  55                  60

Leu Gly Phe Ile Ser Leu Leu Leu Thr Val Gly Gln Gly Leu Ile Ser
65                  70                  75                  80

Thr Ile Cys Ile Ser Lys Ser Val Ala Ala Thr Trp His Pro Cys Ser
                85                  90                  95
```

Lys Ser Glu Glu Glu Lys Ser Thr Thr Thr Glu Glu Ser Asp Thr Glu
            100                 105                 110

Ser Asp Asn Arg Arg Lys Leu Leu Ser Ile Ser Gly Phe Gly Gly Gly
            115                 120                 125

Ser Arg Arg Val Leu Ala Ala Ala Gly Glu Asp Lys Cys Ser Ala Lys
            130                 135                 140

Gly Gln Ala Pro Phe Val Ser Ser Asp Ala Ile His Gln Leu His Ile
145                 150                 155                 160

Phe Ile Phe Val Leu Ala Ile Phe His Val Leu Tyr Cys Ile Leu Thr
                165                 170                 175

Leu Ala Leu Gly Thr Ala Lys Met Arg Arg Trp Lys Ala Trp Glu Lys
            180                 185                 190

Glu Thr Arg Thr Val Glu Tyr Gln Phe Ser His Asp Pro Glu Arg Phe
            195                 200                 205

Arg Phe Ala Arg Glu Thr Ser Phe Gly Arg Arg His Leu Ser Phe Trp
            210                 215                 220

Thr Asn Thr Pro Phe Leu Ile Trp Ile Val Cys Phe Phe Arg Gln Phe
225                 230                 235                 240

Val Arg Ser Val Pro Lys Val Asp Tyr Phe Thr Leu Arg His Gly Phe
                245                 250                 255

Ile Met Ala His Leu Ala Pro Gln Ser His Ala Lys Phe Asp Phe Gln
            260                 265                 270

Lys Tyr Ile Asn Arg Ser Leu Glu Glu Asp Phe Lys Val Val Val Gly
            275                 280                 285

Ile Ser Pro Pro Ile Trp Phe Phe Ala Val Leu Phe Leu Leu Leu Asn
            290                 295                 300

Thr His Gly Trp Tyr Ser Tyr Leu Trp Leu Pro Phe Ile Pro Leu Ile
305                 310                 315                 320

Val Ile Leu Leu Val Gly Thr Lys Leu Gln Val Ile Ile Thr Lys Met
                325                 330                 335

Gly Leu Arg Ile Gln Glu Arg Gly Glu Val Val Lys Gly Val Pro Val
            340                 345                 350

Val Gln Leu Gly Asp Asp Leu Phe Trp Phe Asn Arg Pro Arg Leu Val
            355                 360                 365

Leu Tyr Leu Ile His Phe Val Leu Phe Gln Asn Ala Phe Gln Leu Ala
            370                 375                 380

Phe Phe Ala Trp Thr Trp Tyr Glu Phe Gly Phe Lys Ser Cys Phe Tyr
385                 390                 395                 400

Ala His Thr Glu Asp Val Val Ile Arg Ile Ser Met Gly Val Ile Ile
                405                 410                 415

Gln Ile Leu Cys Ser Tyr Val Thr Leu Pro Leu Tyr Ala Leu Val Thr
            420                 425                 430

Gln Met Gly Ser Thr Met Lys Pro Thr Ile Phe His Glu Arg Val Ala
            435                 440                 445

Thr Ala Leu Arg Asn Trp His His Thr Ala Lys Lys Asn Ile Lys His
            450                 455                 460

Asn Lys His Ser Gly Leu Ala Thr Pro Met Ser Ser Arg Pro Thr Thr
465                 470                 475                 480

Pro Ser Arg Gly Thr Ser Pro Ala Tyr Leu Leu Arg Tyr Tyr Arg Ser
                485                 490                 495

Asp Met Asp Ser Leu Gln Ala Ser Pro Arg Arg Ser Asn Leu Asp Met
            500                 505                 510

Glu His Trp Glu Thr Asp Gly Ser Pro Ser Pro Ser His Pro His His

-continued

```
                515                      520                      525
Gly Asp Gly Ser Ser Ser His His Asn Gln Leu His Gln Gly Thr Ser
        530                      535                      540

Leu Glu His Asp Arg Asp Ile Ser Ala Pro Ser Ser Ser Gln Val Val
545                      550                      555                      560

Pro Leu Pro Gln Pro Thr Leu His Gln His Glu Ile Asp Val Val Arg
                565                      570                      575

Lys Glu Phe Ser Phe Asp Arg Arg Glu Arg
        580                      585

<210> SEQ ID NO 2
<211> LENGTH: 1764
<212> TYPE: DNA
<213> ORGANISM: Vitis vinifera

<400> SEQUENCE: 2
atggctgggg caaccggagg aaggtcgctg gagcagacgc cgacatgggc tgttgctgta      60
gtttgttttg ttttggtgtt gatttctatt atcattgagt acatcattca tctcactgga     120
aagtggttga agaagaaaca caagagagct ctatatgaag cgctggaaaa ggtcaaatca     180
gagctaatgt tgctagggtt catatccttg ctcctaacag taggacaagg tctgatatcg     240
actatatgta tatcaaagag tgttgcagca acttggcatc catgcagcaa gtctgaagaa     300
gagaagagca caacgactga agaatcagac accgaatccg ataatagacg aaaacttctc     360
agcatatcgg gttttggtgg aggcagccga cgcgtttttgg cggcagctgg agaagacaaa     420
tgttcagcta agggtcaagc cccatttgtg tcgtcggatg ctattcacca actgcacata     480
ttcatcttcg tactggccat tttccatgtc ctttactgca tcttaacccct ggctttgggc     540 acagctaaga tgagaaggtg gaaggcatgg gaaaaggaaa caagaacagt cgagtaccag     600
ttctcccacg atccggagag gttcaggttt gccagggaga cgtcttttgg aagaaggcac     660
ttgagtttct ggaccaatac acccttttctc atctggatag tatgtttctt cagacagttc     720
gttaggtccg ttccaaaagt tgactacttc accttaagac atggatttat catggcacat     780
ttggcacctc aaagccatgc aaaatttgat ttccaaaaat atatcaatag atcgctggag     840
gaggatttca aggtggttgt gggtatcagt ccaccaatat ggttctttgc cgtgctattc     900
cttctcctca acactcatgg ctggtactct tatctatggc tgccattcat cccactgatt     960
gttatcctat tggtgggaac caagttacag gtgatcataa ccaagatggg gcttagaatt    1020
caagaaaggg gagaggttgt gaagggagtg ccggttgttc agcttggtga tgacctcttc    1080
tggttcaatc gccctcgcct cgttctctac ctcatccatt ttgtgctctt tcagaacgca    1140
tttcagctgg ctttcttcgc atggacttgg tatgaattcg ggtttaagtc ttgtttctat    1200
gcacacactg aagatgtggt gatcaggatt tccatggggg tcatcataca gattctttgc    1260
agctacgtaa ctctcccgct ctatgccctg gtgacacaga tgggttcaac catgaagcca    1320
acgatcttcc atgagagagt agccacggct ctaaggaact ggcaccacac ggctaagaaa    1380
aacatcaaac acaacaagca ttctgggcta gccacaccca tgtcaagtag gccaacaacg    1440
ccttcccgcg gcacgtcccc tgcttacctc ttgcgctact accggagcga catggacagc    1500
ctccaagcat ccccgagaag gtccaacttg gacatggagc attgggagac tgatgggtcc    1560 ccctcccccct cgcacccgca ccatggtgac ggctcatcct ctcaccacaa ccagctccac    1620
caaggaacgt ccttggaaca tgatagagac atcagcgcgc ctagctcctc ccaagtggtt    1680
cctcttccac aacccactct ccaccaacac gaaatcgatg ttgtgcgcaa ggaatttttca    1740
```

-continued

```
tttgatcgaa gagagaggac gtga                                               1764

<210> SEQ ID NO 3
<211> LENGTH: 1763
<212> TYPE: DNA
<213> ORGANISM: Vitis vinifera

<400> SEQUENCE: 3
atggctgggg caaccggagg aaggtcgctg gagcagacgc cgacatgggc tgttgctgta        60
gtttgttttg ttttggtgtt gatttctatt atcattgagt acatcattca tctcactgga       120
aagtggttga agaagaaaca caagagagct ctatatgaag cgctggaaaa ggtcaaatca       180
gagctaatgt tgctagggtt catatccttg ctcctaacag taggacaagg tctgatatcg       240
actatatgta tatcaaagag tgttgcagca acttggcatc catgcagcaa gtctgaagaa       300
gagaagagca caacgactga agaatcagac accgaatccg ataatagacg aaaacttctc       360
agcatatcgg gttttggtgg aggcagccga cgcgttttgg cggcagctgg agaagacaaa       420
tgttcagcta agggtcaagc cccatttgtg tcgtcggatg ctattcacca actgcacata       480
ttcatcttcg tactggccat tttccatgtc ctttactgca tcttaaccct ggctttgggc       540
acagctaaga tgagaaggtg gaaggcatgg gaaaaggaaa caagaacagt cgagtaccag       600
ttctcccacg atccggagag gttcaggttt gccagggaga cgtcttttgg aagaaggcac       660
ttgagtttct ggaccaatac accctttctc atctggatag tatgtttctt cagacagttc       720
gttaggtccg ttccaaaagt tgactacttc accttaagac atggatttat catggcacat       780
ttggcacctc aaagccatgc aaaatttgat ttccaaaaat atatcaatag atcgctggag       840
gaggatttca aggtggttgt gggtatcagt ccaccaatat ggttctttgc cgtgctattc       900
cttctcctca acactcatgg ctggtactct tatctatggc tgccattcat cccactgatt       960
gttatcctat tggtgggaac caagttacag gtgatcataa ccaagatggg gcttagaatt      1020
caagaaaggg gagaggttgt gaagggagtg ccggttgttc agcttggtga tgacctcttc      1080
tggttcaatc gccctcgcct cgttctctac ctcatccatt ttgtgctctt tcagaacgca      1140
tttcagctgg ctttcttcgc atggacttgg tatgaattcg ggtttaagtc ttgtttctat      1200
gcacacactg aagatgtggt gatcaggatt tccatggggg tcatcataca gattctttgc      1260
agctacgtaa ctctcccgct ctatgccctg gtgacacaga tgggttcaac catgaagcca      1320
acgatcttcc atgagagagt agccacggct ctaaggaact ggcaccacac ggctaagaaa      1380
aacatcaaac acaacaagca ttctgggcta gccacaccca tgtcaagtag gccaacacgc      1440
cttcccgcgg cacgtcccct gcttacctct tgcgctacta ccggagcgac atggacagcc      1500
tccaagcatc cccgagaagg tccaacttgg acatggagca ttgggagact gatgggtccc      1560 cctcccctc gcacccgcac catggtgacg gctcatcctc tcaccacaac cagctccacc      1620
aaggaacgtc cttggaacat gatagagaca tcagcgcgcc tagctcctcc caagtggttc      1680
ctcttccaca acccactctc caccaacacg aaatcgatgt tgtgcgcaag gaattttcat      1740
ttgatcgaag agagaggacg tga                                              1763

<210> SEQ ID NO 4
<211> LENGTH: 1761
<212> TYPE: DNA
<213> ORGANISM: Vitis vinifera

<400> SEQUENCE: 4
```

-continued

```
atggctgggg caaccggagg aaggtcgctg gagcagacgc cgacatgggc tgttgctgta        60
gtttgttttg ttttggtgtt gatttctatt atcattgagt acatcattca tctcactgga       120
aagtggttga agaagaaaca caagagagct ctatatgaag cgctggaaaa ggtcaaatca       180
gagctaatgt tgctagggtt catatccttg ctcctaacag taggacaagg tctgatatcg       240
actatatgta tatcaaagag tgttgcagca acttggcatc catgcagcaa gtctgaagaa       300
gagaagagca caacgactga agaatcagac accgaatccg ataatagacg aaaacttctc       360
agcatatcgg gttttggtgg aggcagccga cgcgtttttgg cggcagctgg agaagacaaa      420
tgttcagcta agggtcaagc cccatttgtg tcgtcggatg ctattcacca actgcacata       480
ttcatcttcg tactggccat tttccatgtc ctttactgca tcttaaccct ggctttgggc       540
acagctaaga tgagaaggtg gaaggcatgg gaaaaggaaa caagaacagt cgagtaccag       600
ttctcccacg atccggagag gttcaggttt gccagggaga cgtctttttgg aagaaggcac      660 ttgagtttct ggaccaatac accctttctc atctggatag tatgtttctt cagacagttc       720
gttaggtccg ttccaaaagt tgactacttc accttaagac atggatttat catggcacat       780
ttggcacctc aaagccatgc aaaatttgat ttccaaaaat atatcaatag atcgctggag       840
gaggatttca aggtggttgt gggtatcagt ccaccaaat ggttctttgc cgtgctattc       900
cttctcctca acactcatgg ctggtactct tatctatggc tgccattcat cccactgatt       960
gttatcctat tggtgggaac caagttacag gtgatcataa ccaagatggg gcttagaatt      1020
caagaaaggg gagaggttgt gaagggagtg ccggttgttc agcttggtga tgacctcttc      1080
tggttcaatc gccctcgcct cgttctctac ctcatccatt ttgtgctctt tcagaacgca      1140
tttcagctgg ctttcttcgc atggacttgg tatgaattcg ggtttaagtc ttgtttctat      1200
gcacacactg aagatgtggt gatcaggatt tccatggggg tcatcataca gattctttgc      1260
agctacgtaa ctctcccgct ctatgccctg gtgacacaga tgggttcaac catgaagcca      1320
acgatcttcc atgagagagt agccacggct ctaaggaact ggcaccacac ggctaagaaa      1380
aacatcaaac acaacaagca ttctgggcta gccacaccca tgtcaagtag gccaacgcct      1440
tcccgcggca cgtcccctgc ttacctcttg cgctactacc ggagcgacat ggacagcctc      1500
caagcatccc cgagaaggtc caacttggac atggagcatt gggagactga tgggtccccc      1560 tcccctcgc acccgcacca tggtgacggc tcatcctctc accacaacca gctccaccaa      1620
ggaacgtcct tggaacatga tagagacatc agcgcgccta gctcctccca agtggttcct      1680
cttccacaac ccactctcca ccaacacgaa atcgatgttg tgcgcaagga attttcattt      1740
gatcgaagag agaggacgtg a                                              1761
```

```
<210> SEQ ID NO 5
<211> LENGTH: 1765
<212> TYPE: DNA
<213> ORGANISM: Vitis vinifera

<400> SEQUENCE: 5
```

```
atggctgggg caaccggagg aaggtcgctg gagcagacgc cgacatgggc tgttgctgta        60
gtttgttttg ttttggtgtt gatttctatt atcattgagt acatcattca tctcactgga       120
aagtggttga agaagaaaca caagagagct ctatatgaag cgctggaaaa ggtcaaatca       180
gagctaatgt tgctagggtt catatccttg ctcctaacag taggacaagg tctgatatcg       240
actatatgta tatcaaagag tgttgcagca acttggcatc catgcagcaa gtctgaagaa       300
gagaagagca caacgactga agaatcagac accgaatccg ataatagacg aaaacttctc       360
```

-continued

```
agcatatcgg gttttggtgg aggcagccga cgcgttttgg cggcagctgg agaagacaaa      420
tgttcagcta agggtcaagc cccatttgtg tcgtcggatg ctattcacca actgcacata      480
ttcatcttcg tactggccat tttccatgtc ctttactgca tcttaaccct ggctttgggc      540
acagctaaga tgagaaggtg gaaggcatgg gaaaaggaaa caagaacagt cgagtaccag      600
ttctcccacg atccggagag gttcaggttt gccagggaga cgtcttttgg aagaaggcac      660
ttgagtttct ggaccaatac accctttctc atctggatag tatgtttctt cagacagttc      720
gttaggtccg ttccaaaagt tgactacttc accttaagac atggatttat catggcacat      780
ttggcacctc aaagccatgc aaaatttgat ttccaaaaat atatcaatag atcgctggag      840
gaggatttca aggtggttgt gggtatcagt ccaccaatat ggttctttgc cgtgctattc      900
cttctcctca acactcatgg ctggtactct tatctatggc tgccattcat cccactgatt      960
gttatcctat tggtgggaac caagttacag gtgatcataa ccaagatggg gcttagaatt     1020
caagaaaggg gagaggttgt gaagggagtg ccggttgttc agcttggtga tgacctcttc     1080
tggttcaatc gccctcgcct cgttctctac ctcatccatt ttgtgctctt tcagaacgca     1140
tttcagctgg ctttcttcgc atggacttgg tatgaattcg ggtttaagtc ttgtttctat     1200
gcacacactg aagatgtggt gatcaggatt tccatggggg tcatcataca gattctttgc     1260
agctacgtaa ctctcccgct ctatgccctg gtgacacaga tgggttcaac catgaagcca     1320
acgatcttcc atgagagagt agccacggct ctaaggaact ggcaccacac ggctaagaaa     1380
aacatcaaac acaacaagca ttctgggcta gccacaccca tgtcaagtag gccaacatac     1440
gccttcccgc ggcacgtccc ctgcttacct cttgcgctac taccggagcg acatggacag     1500
cctccaagca tccccgagaa ggtccaactt ggacatggag cattgggaga ctgatgggtc     1560
cccctccccc tcgcacccgc accatggtga cggctcatcc tctcaccaca accagctcca     1620
ccaaggaacg tccttggaac atgatagaga catcagcgcg cctagctcct cccaagtggt     1680
tcctcttcca caacccactc tccaccaaca cgaaatcgat gttgtcgca aggaattttc      1740 atttgatcga agagagagga cgtga                                          1765
```

<210> SEQ ID NO 6
<211> LENGTH: 587
<212> TYPE: PRT
<213> ORGANISM: Vitis vinifera

<400> SEQUENCE: 6

```
Met Ala Gly Ala Thr Gly Gly Arg Ser Leu Glu Gln Thr Pro Thr Trp
1               5                   10                  15

Ala Val Ala Val Val Cys Phe Val Leu Val Leu Ile Ser Ile Ile Ile
            20                  25                  30

Glu Tyr Ile Ile His Leu Thr Gly Lys Trp Leu Lys Lys Lys His Lys
        35                  40                  45

Arg Ala Leu Tyr Glu Ala Leu Glu Lys Val Lys Ser Glu Leu Met Leu
    50                  55                  60

Leu Gly Phe Ile Ser Leu Leu Leu Thr Val Gly Gln Gly Leu Ile Ser
65                  70                  75                  80

Thr Ile Cys Ile Ser Lys Ser Val Ala Ala Thr Trp His Pro Cys Ser
                85                  90                  95

Lys Ser Glu Glu Glu Lys Ser Thr Thr Thr Glu Glu Ser Asp Thr Glu
            100                 105                 110

Ser Asp Asn Arg Arg Lys Leu Leu Ser Ile Ser Gly Phe Gly Gly Gly
```

```
              115                 120                 125

Ser Arg Arg Val Leu Ala Ala Ala Gly Glu Asp Lys Cys Ser Ala Lys
    130                 135                 140

Gly Gln Ala Pro Phe Val Ser Ser Asp Ala Ile His Gln Leu His Ile
145                 150                 155                 160

Phe Ile Phe Val Leu Ala Ile Phe His Val Leu Tyr Cys Ile Leu Thr
                165                 170                 175

Leu Ala Leu Gly Thr Ala Lys Met Arg Arg Trp Lys Ala Trp Glu Lys
                180                 185                 190

Glu Thr Arg Thr Val Glu Tyr Gln Phe Ser His Asp Pro Glu Arg Phe
                195                 200                 205

Arg Phe Ala Arg Glu Thr Ser Phe Gly Arg Arg His Leu Ser Phe Trp
    210                 215                 220

Thr Asn Thr Pro Phe Leu Ile Trp Ile Val Cys Phe Phe Arg Gln Phe
225                 230                 235                 240

Val Arg Ser Val Pro Lys Val Asp Tyr Phe Thr Leu Arg His Gly Phe
                245                 250                 255

Ile Met Ala His Leu Ala Pro Gln Ser His Ala Lys Phe Asp Phe Gln
                260                 265                 270

Lys Tyr Ile Asn Arg Ser Leu Glu Glu Asp Phe Lys Val Val Val Gly
                275                 280                 285

Ile Ser Pro Pro Ile Trp Phe Phe Ala Val Leu Phe Leu Leu Leu Asn
    290                 295                 300

Thr His Gly Trp Tyr Ser Tyr Leu Trp Leu Pro Phe Ile Pro Leu Ile
305                 310                 315                 320

Val Ile Leu Leu Val Gly Thr Lys Leu Gln Val Ile Ile Thr Lys Met
                325                 330                 335

Gly Leu Arg Ile Gln Glu Arg Gly Glu Val Val Lys Gly Val Pro Val
                340                 345                 350

Val Gln Leu Gly Asp Asp Leu Phe Trp Phe Asn Arg Pro Arg Leu Val
                355                 360                 365

Leu Tyr Leu Ile His Phe Val Leu Phe Gln Asn Ala Phe Gln Leu Ala
    370                 375                 380

Phe Phe Ala Trp Thr Trp Tyr Glu Phe Gly Phe Lys Ser Cys Phe Tyr
385                 390                 395                 400

Ala His Thr Glu Asp Val Val Ile Arg Ile Ser Met Gly Val Ile Ile
                405                 410                 415

Gln Ile Leu Cys Ser Tyr Val Thr Leu Pro Leu Tyr Ala Leu Val Thr
                420                 425                 430

Gln Met Gly Ser Thr Met Lys Pro Thr Ile Phe His Glu Arg Val Ala
    435                 440                 445

Thr Ala Leu Arg Asn Trp His His Thr Ala Lys Lys Asn Ile Lys His
    450                 455                 460

Asn Lys His Ser Gly Leu Ala Thr Pro Met Ser Ser Arg Pro Thr Arg
465                 470                 475                 480

Leu Pro Ala Ala Arg Pro Leu Leu Thr Ser Cys Ala Thr Thr Gly Ala
                485                 490                 495

Thr Trp Thr Ala Ser Lys His Pro Arg Glu Gly Pro Thr Trp Thr Trp
                500                 505                 510

Ser Ile Gly Arg Leu Met Gly Pro Pro Pro Arg Thr Arg Thr Met
                515                 520                 525

Val Thr Ala His Pro Leu Thr Thr Thr Ser Ser Thr Lys Glu Arg Pro
    530                 535                 540
```

```
Trp Asn Met Ile Glu Thr Ser Ala Arg Leu Ala Pro Pro Lys Trp Phe
545                 550                 555                 560

Leu Phe His Asn Pro Leu Ser Thr Asn Thr Lys Ser Met Leu Cys Ala
                565                 570                 575

Arg Asn Phe His Leu Ile Glu Glu Arg Gly Arg
                580                 585

<210> SEQ ID NO 7
<211> LENGTH: 586
<212> TYPE: PRT
<213> ORGANISM: Vitis vinifera

<400> SEQUENCE: 7

Met Ala Gly Ala Thr Gly Gly Arg Ser Leu Glu Gln Thr Pro Thr Trp
1                   5                   10                  15

Ala Val Ala Val Val Cys Phe Val Leu Val Leu Ile Ser Ile Ile Ile
                20                  25                  30

Glu Tyr Ile Ile His Leu Thr Gly Lys Trp Leu Lys Lys Lys His Lys
            35                  40                  45

Arg Ala Leu Tyr Glu Ala Leu Glu Lys Val Lys Ser Glu Leu Met Leu
        50                  55                  60

Leu Gly Phe Ile Ser Leu Leu Leu Thr Val Gly Gln Gly Leu Ile Ser
65                  70                  75                  80

Thr Ile Cys Ile Ser Lys Ser Val Ala Ala Thr Trp His Pro Cys Ser
                85                  90                  95

Lys Ser Glu Glu Glu Lys Ser Thr Thr Thr Glu Glu Ser Asp Thr Glu
                100                 105                 110

Ser Asp Asn Arg Arg Lys Leu Leu Ser Ile Ser Gly Phe Gly Gly Gly
            115                 120                 125

Ser Arg Arg Val Leu Ala Ala Ala Gly Glu Asp Lys Cys Ser Ala Lys
        130                 135                 140

Gly Gln Ala Pro Phe Val Ser Ser Asp Ala Ile His Gln Leu His Ile
145                 150                 155                 160

Phe Ile Phe Val Leu Ala Ile Phe His Val Leu Tyr Cys Ile Leu Thr
                165                 170                 175

Leu Ala Leu Gly Thr Ala Lys Met Arg Arg Trp Lys Ala Trp Glu Lys
            180                 185                 190

Glu Thr Arg Thr Val Glu Tyr Gln Phe Ser His Asp Pro Glu Arg Phe
            195                 200                 205

Arg Phe Ala Arg Glu Thr Ser Phe Gly Arg Arg His Leu Ser Phe Trp
        210                 215                 220

Thr Asn Thr Pro Phe Leu Ile Trp Ile Val Cys Phe Phe Arg Gln Phe
225                 230                 235                 240

Val Arg Ser Val Pro Lys Val Asp Tyr Phe Thr Leu Arg His Gly Phe
                245                 250                 255

Ile Met Ala His Leu Ala Pro Gln Ser His Ala Lys Phe Asp Phe Gln
            260                 265                 270

Lys Tyr Ile Asn Arg Ser Leu Glu Glu Asp Phe Lys Val Val Val Gly
            275                 280                 285

Ile Ser Pro Pro Ile Trp Phe Phe Ala Val Leu Phe Leu Leu Leu Asn
        290                 295                 300

Thr His Gly Trp Tyr Ser Tyr Leu Trp Leu Pro Phe Ile Pro Leu Ile
305                 310                 315                 320

Val Ile Leu Leu Val Gly Thr Lys Leu Gln Val Ile Ile Thr Lys Met
```

-continued

```
                325                 330                 335

Gly Leu Arg Ile Gln Glu Arg Gly Glu Val Val Lys Gly Val Pro Val
            340                 345                 350

Val Gln Leu Gly Asp Asp Leu Phe Trp Phe Asn Arg Pro Arg Leu Val
            355                 360                 365

Leu Tyr Leu Ile His Phe Val Leu Phe Gln Asn Ala Phe Gln Leu Ala
            370                 375                 380

Phe Phe Ala Trp Thr Trp Tyr Glu Phe Gly Phe Lys Ser Cys Phe Tyr
385                 390                 395                 400

Ala His Thr Glu Asp Val Val Ile Arg Ile Ser Met Gly Val Ile Ile
            405                 410                 415

Gln Ile Leu Cys Ser Tyr Val Thr Leu Pro Leu Tyr Ala Leu Val Thr
            420                 425                 430

Gln Met Gly Ser Thr Met Lys Pro Thr Ile Phe His Glu Arg Val Ala
            435                 440                 445

Thr Ala Leu Arg Asn Trp His His Thr Ala Lys Lys Asn Ile Lys His
            450                 455                 460

Asn Lys His Ser Gly Leu Ala Thr Pro Met Ser Ser Arg Pro Thr Pro
465                 470                 475                 480

Ser Arg Gly Thr Ser Pro Ala Tyr Leu Leu Arg Tyr Tyr Arg Ser Asp
            485                 490                 495

Met Asp Ser Leu Gln Ala Ser Pro Arg Arg Ser Asn Leu Asp Met Glu
            500                 505                 510

His Trp Glu Thr Asp Gly Ser Pro Ser Pro Ser His Pro His His Gly
            515                 520                 525

Asp Gly Ser Ser Ser His His Asn Gln Leu His Gln Gly Thr Ser Leu
            530                 535                 540

Glu His Asp Arg Asp Ile Ser Ala Pro Ser Ser Ser Gln Val Val Pro
545                 550                 555                 560

Leu Pro Gln Pro Thr Leu His Gln His Glu Ile Asp Val Val Arg Lys
            565                 570                 575

Glu Phe Ser Phe Asp Arg Arg Glu Arg Thr
            580                 585

<210> SEQ ID NO 8
<211> LENGTH: 517
<212> TYPE: PRT
<213> ORGANISM: Vitis vinifera

<400> SEQUENCE: 8

Met Ala Gly Ala Thr Gly Gly Arg Ser Leu Glu Gln Thr Pro Thr Trp
1                 5                   10                  15

Ala Val Ala Val Val Cys Phe Val Leu Val Leu Ile Ser Ile Ile Ile
            20                  25                  30

Glu Tyr Ile Ile His Leu Thr Gly Lys Trp Leu Lys Lys Lys His Lys
            35                  40                  45

Arg Ala Leu Tyr Glu Ala Leu Glu Lys Val Lys Ser Glu Leu Met Leu
            50                  55                  60

Leu Gly Phe Ile Ser Leu Leu Leu Thr Val Gly Gln Gly Leu Ile Ser
65                  70                  75                  80

Thr Ile Cys Ile Ser Lys Ser Val Ala Ala Thr Trp His Pro Cys Ser
            85                  90                  95

Lys Ser Glu Glu Glu Lys Ser Thr Thr Thr Glu Glu Ser Asp Thr Glu
            100                 105                 110
```

-continued

```
Ser Asp Asn Arg Arg Lys Leu Leu Ser Ile Ser Gly Phe Gly Gly Gly
        115                 120             125

Ser Arg Arg Val Leu Ala Ala Ala Gly Glu Asp Lys Cys Ser Ala Lys
        130             135             140

Gly Gln Ala Pro Phe Val Ser Ser Asp Ala Ile His Gln Leu His Ile
145                 150             155                 160

Phe Ile Phe Val Leu Ala Ile Phe His Val Leu Tyr Cys Ile Leu Thr
                165             170             175

Leu Ala Leu Gly Thr Ala Lys Met Arg Arg Trp Lys Ala Trp Glu Lys
            180             185             190

Glu Thr Arg Thr Val Glu Tyr Gln Phe Ser His Asp Pro Glu Arg Phe
            195             200             205

Arg Phe Ala Arg Glu Thr Ser Phe Gly Arg Arg His Leu Ser Phe Trp
        210             215             220

Thr Asn Thr Pro Phe Leu Ile Trp Ile Val Cys Phe Phe Arg Gln Phe
225             230             235                 240

Val Arg Ser Val Pro Lys Val Asp Tyr Phe Thr Leu Arg His Gly Phe
                245             250             255

Ile Met Ala His Leu Ala Pro Gln Ser His Ala Lys Phe Asp Phe Gln
            260             265             270

Lys Tyr Ile Asn Arg Ser Leu Glu Glu Asp Phe Lys Val Val Val Gly
        275             280             285

Ile Ser Pro Pro Ile Trp Phe Phe Ala Val Leu Phe Leu Leu Leu Asn
        290             295             300

Thr His Gly Trp Tyr Ser Tyr Leu Trp Leu Pro Phe Ile Pro Leu Ile
305             310             315                 320

Val Ile Leu Leu Val Gly Thr Lys Leu Gln Val Ile Ile Thr Lys Met
                325             330             335

Gly Leu Arg Ile Gln Glu Arg Gly Glu Val Val Lys Gly Val Pro Val
            340             345             350

Val Gln Leu Gly Asp Asp Leu Phe Trp Phe Asn Arg Pro Arg Leu Val
            355             360             365

Leu Tyr Leu Ile His Phe Val Leu Phe Gln Asn Ala Phe Gln Leu Ala
        370             375             380

Phe Phe Ala Trp Thr Trp Tyr Glu Phe Gly Phe Lys Ser Cys Phe Tyr
385             390             395                 400

Ala His Thr Glu Asp Val Val Ile Arg Ile Ser Met Gly Val Ile Ile
                405             410             415

Gln Ile Leu Cys Ser Tyr Val Thr Leu Pro Leu Tyr Ala Leu Val Thr
            420             425             430

Gln Met Gly Ser Thr Met Lys Pro Thr Ile Phe His Glu Arg Val Ala
            435             440             445

Thr Ala Leu Arg Asn Trp His His Thr Ala Lys Lys Asn Ile Lys His
        450             455             460

Asn Lys His Ser Gly Leu Ala Thr Pro Met Ser Ser Arg Pro Thr Tyr
465             470             475                 480

Ala Phe Pro Arg His Val Pro Cys Leu Pro Leu Ala Leu Leu Pro Glu
                485             490             495

Arg His Gly Gln Pro Pro Ser Ile Pro Glu Lys Val Gln Leu Gly His
            500             505             510

Gly Ala Leu Gly Asp
            515
```